United States Patent [19]

Chamberlin, Sr.

[11] Patent Number: Plant 6,077

[45] Date of Patent: Jan. 5, 1988

[54] PLUM TREE, "ANNA SUN"

[75] Inventor: Thomas O. Chamberlin, Sr., Visalia, Calif.

[73] Assignee: Metzler Investments and Metropolitan Life Insurance Company, Del Rey, Calif.

[21] Appl. No.: 782,469

[22] Filed: Oct. 1, 1985

[51] Int. Cl.[4] ..... A01H 5/03

[52] U.S. Cl. ..... Plt./38

[58] Field of Search ..... Plt./38

*Primary Examiner*—Robert E. Bagwill

*Attorney, Agent, or Firm*—Worrel & Worrel

[57] ABSTRACT

A new and distinct variety of plum tree which is somewhat similar to the Kelsey Plum Tree (unpatented), with which it is generally similar to physical characteristics but from which it is distinguished by bearing a Medium Green colored fruit with a yellow flesh which matures for harvesting approximately three weeks later than the Kelsey Plum Tree.

1 Drawing Figure

BACKGROUND OF THE NEW VARIETY

The present invention relates to a new and distinct variety of plum tree, which has been denominated varietally as "Anna Sun", and which is broadly similar to the Kelsey Plum Tree (unpatented), with which it is most similar in appearance, but from which it is distinguished in being ready for harvest about 3 weeks later than in the Kelsey Plum Tree, and by producing a fruit which has a Medium Green skin color with a Yellow-colored flesh.

The applicant, in an effort to upgrade the fruit products of his employer, has germinated thousands of plum seeds of random parentage, grown the resultant seedlings to maturity and carefully studied the characteristics of the progeny in an effort to discover new and superior varieties of plums. The subject variety was discovered as a result of this procedure.

ORIGIN AND ASEXUAL REPRODUCTION OF THE NEW VARIETY

The seedling of the present variety was the offspring of unknown parents, and was produced from a mixed lot of seeds which were procured from the H. P. Metzler & Sons Ranch No. 5, located in Del Rey, Calif. The mixed lot of seeds which were produced from Ranch No. 5 were planted in the H. P. Metzler & Sons nursery, located at the aforementioned ranch, during the winter of 1979 and 1980. The seedling of the instant variety first produced fruit in 1982. The special qualities of the subject variety were detected and appreciated in 1982 because the fruit that was produced by the seedling had a Green skin color. This was particularly unique in that the seeds which were procured from Ranch No. 5 came from plum trees which produced either black or dark red plums. Upon detection of this unique seedling, budwood was taken from it, and was budded to stock trees in the H. P. Metzler & Sons test area of the nursery in 1983. These budded trees produced their first fruit in August of 1984. The budded progeny have dependably and accurately reproduced the superior characteristics observed by the applicant in the original seedling.

BRIEF DESCRIPTION OF THE DRAWING

The accompanying drawing in a color photograph of a characteristic twig bearing typical leaves, several plums showing their external coloration sufficiently mature for harvest and shipment, a plum halved transversely of the suture plane to illustrate the flesh coloration, and two stones, all of the subject variety.

DETAILED DESCRIPTION

Referring more particularly to the pomological details of this new and distinct variety of plum tree, the following has been observed under the ecological conditions prevailing in the designated orchards near Del Rey, Calif. All major color code designations are by reference to Inter-Society Color Council, National Bureau of Standards. Common color names are also used occasionally.

TREE

Size: Average, depending upon pruning practices.
Vigor: Vigorous.
Figure: Normal, and upright.
Productivity: Productive.
Regularity of bearing: Heavy, regular.
Trunk:
- *Diameter.*—Normal.
- *Surface texture.*—Average Plum Tree bark.
- *Lenticels.*—Approximately 22 through 25 lenticels per square inch.
- *Color.*—62 d. gy. Br.

Branches:
- *Size.*—Average.
- *Surface texture.*—Same characteristics as the trunk.
- *Color.*—62 d. gy. Br.
- *Lenticels.*—Number — approximately 22 through 25 per square inch. Size — small.

LEAVES

Size: Average.
Length: Approximately 2½ inches to 2¾ inches, (63.5 mm through 69.85 mm).
Width: Approximately 1¾ inches to 2 inches, (44.45 mm through 50.8 mm).
Color:
- *Dorsal side.*—125 m. 01.G.
- *Ventral side.*—122 gy. Y. G.

Shape: Ovate.
Marginal form: Doubly serrate.
Shape of glands: Globose.
Petiole:

*Length.*—Approximately ½ inch, (12.7 mm).
*Thickness.*—Approximately 1/16 inch (1.588 mm).

Stem glands:
*Number.*—One pair.
*Arrangement.*—The pair is generally opposed to each other.

Stipules:
*Number.*—One pair.
*Position.*—Located at the base of the petiole.

Flower Buds:
*Size.*—Diameter — approximately ⅛ inch (3.175 mm); Length — approximately ⅛ inch (3.175 mm).
*Petiole.*—Approximately ⅛ inch, (3.175 mm), at the time prior to the appearance of any white in the flower bud.
*Shape.*—Small and round, at the time prior to the appearance of any color in the bud.
*Bud development.*—Each bud develops by itself.
*Position of buds.*—The buds of the subject variety are positioned in clusters.
*Color of bud.*—116-brille Y.G., this color appears at a time prior to the appearance of any white color in the apex area of the bud.

Flowers:
*Date of bloom.*—Four to five days after the Santa Rosa (unpatented), approximately March 1 through March 5 in Del Rey, Calif.
*Size.*—Length of each petal — approximately ⅜ inch, (9.525 mm).
*Diameter.*—Approximately ¼ inch (6.35 mm).
*Color.*—#263 White.
*Stem length.*—Approximately ½ inch, (12.7 mm), when the flower is fully open.
*Shape of petals.*—Elongated and small.
*Form of flower.*—Small, with a very heavy, solid blossom.

FRUIT

Maturity when described: Ripe for harvesting, August 12–15, at Del Rey, Calif.

Size:
*Uniformity.*—Good.
*Diameter.*—Approximately 2-3/16 inches to 2⅜ inches (55.562 through 60.325 mm), although occasionally larger ones may be found.
*Diameter transverse in suture plane.*—2⅜ inches through 2½ inches (60.325 mm through 63.50 mm).
*Diameter transverse in cheek plane.*—2-3/16 inches to 2⅜ inches (55.562 mm through 60.325 mm).

Form:
*Uniformity.*—Good.
*Shape.*—Slightly elongated.
*Suture.*—Prominent and smooth.
*Length of suture.*—Approximately 3½ inches (88.9 mm); the suture extends from the base to the apex.
*Ventral surface.*—Slightly pointed.
*Stem cavity.*—Shape — rounded, approximately ⅛ inch to 3/16 inch deep, (3.175 mm through 4.762 mm).
*Base.*—Rounded.
*Apex.*—Elongated.
*Pistil point.*—Very prominent.

Stem:
*Length.*—Approximately ¾ inch long, (19.050 mm).
*Width.*—Approximately 1/16 inch, (1.588 mm).

Skin:
*Thickness.*—Less than 1/64 inch, (0.397 mm).
*Texture.*—Smooth.
*Tenacious to flesh.*—Yes.
*Tendency to crack.*—None observed.
*Color.*—Medium Green (119 1. Y. G.).

Flesh:
*Color.*—Yellowish-Green (101 1.g. Y.).
*Texture of pit well.*—Slightly rough.
*Color of pit well.*—Same as flesh, (101 1.g. Y.)
*Juice production.*—Very juicy.
*Taste.*—Slightly tart, but pleasant.
*Flavor.*—Excellent, slightly crisp.
*Aroma.*—Slight.
*General texture.*—Smooth and crisp.
*Fibers.*—None evident.
*Ripening.*—Even.
*Eating quality.*—Excellent.
*Storage quality.*—Excellent, the subject variety has been tested, and stored for over three weeks in normal cold storage with no deleterious effects noted.
*Self-pollinating.*—At the present time, the new variety appears to be self-pollinating, and may have the ability to aid other plum trees to produce a crop.

Stone:
*Free or clingstone.*—Almost full freestone.
*Fibers.*—None evident.
*Size.*—Length — approximately 1 inch, (25.4 mm); Width — approximately 9/16 inch, (14.288 mm); Thickness — approximately 5/16 inch, (7.938 mm).
*Form.*—Generally elongated.
*Base shape.*—Almost pointed, however not flat.
*Texture.*—Almost smooth, slightly rough.
*Ridges.*—None.

Usage of plum: Fresh market.
Keeping quality: Excellent.
Shipping quality: All appearances indicate that the shipping qualities are excellent.

Although the new variety of plum tree possesses the described characteristics as a result of the growing conditions in Del Rey, Calif., in the central part of the San Joaquin Valley, it is to be understood that variations of the usual magnitude in characteristics incident to growing conditions, fertilization, pruning and pest control are to be expected.

Having thus described and illustrated my new variety of plum tree, what is claimed as new and desired to be secured by Letters Patent is:

1. A new and distinct variety of plum tree, substantially as illustrated and described, which is somewhat similar to the Kelsey Plum Tree (unpatented), with which it bears fruit which is similar in physical characteristics, but from which it is distinguished by bearing fruit which is mature for harvesting approximately three weeks later than the Kelsey Plum Tree, and has a Medium Green skin color with a yellow flesh, and is generally freestone in nature.

* * * * *

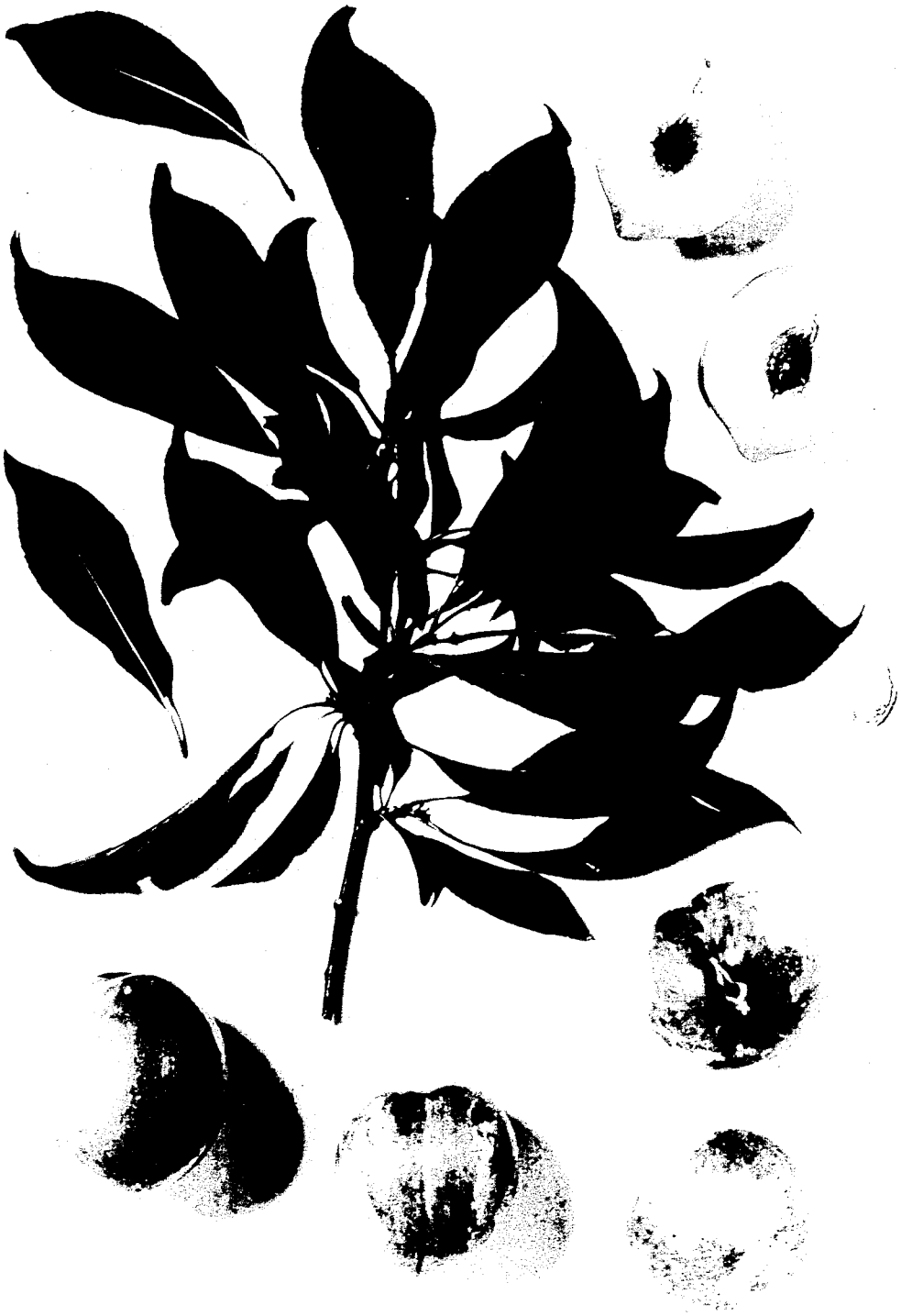

UNITED STATES PATENT AND TRADEMARK OFFICE

CERTIFICATE OF CORRECTION

PATENT NO. : Plant 6,Ø77

DATED : January 5, 1988

INVENTOR(S) :

It is certified that error appears in the above-identified patent and that said Letters Patent is hereby corrected as shown below:

Column 1, line 22, delete "produced" and substitute ---procured---.

Column 1, line 26, delete "produced" and substitute ---procured---.

Signed and Sealed this

Twelfth Day of July, 1988

*Attest:*

DONALD J. QUIGG

*Attesting Officer*

*Commissioner of Patents and Trademarks*